United States Patent
Tsuda et al.

(10) Patent No.: US 6,576,811 B1
(45) Date of Patent: *Jun. 10, 2003

(54) TRANSGENIC RAT WITH HUMAN NORMAL TYPE C-HA-RAS GENE

(75) Inventors: Hiroyuki Tsuda, Tokyo (JP); Makoto Asamoto, Aichi (JP); Hiroyasu Toriyama, Chiba (JP); Takahiro Ochiya, Tokyo (JP); Takeo Sekiya, Kanagawa (JP)

(73) Assignees: National Cancer Center Research Institute, Tokyo (JP); Japan Science and Technology Corporation, Saitama (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 431 days.

(21) Appl. No.: 09/140,197

(22) Filed: Aug. 26, 1998

(30) Foreign Application Priority Data

Feb. 25, 1998 (JP) .......................................... 10-062130

(51) Int. Cl.$^7$ ................................................ G01N 33/00
(52) U.S. Cl. .............................. 800/3; 800/10; 800/13; 800/18
(58) Field of Search ............................ 800/3, 8, 10, 14, 800/18

(56) References Cited

PUBLICATIONS

Voet and Voet. In: Biochemistry, Second Edition. John Wiley and Sons, Publishers. pp. 1154–1159, 1995.*

Katsuki et al. Chemically –induced tumors in transgenic mice carrying prototype human c–Ha–ras genes. Princess Takamatsu Symposia. 22: 249–257, abstract only, 1991.*

Engelbergs et al. Overall and gene–specific repair of DNA O–alkylation products: relevance for mutagenesis and carcinogenic risk (Meeting Abstract). Molecular Aspects of Carcinogenesis, International Meeting. p. 50, abstract only, Sep. 1995.*

* cited by examiner

*Primary Examiner*—James Ketter
*Assistant Examiner*—Richard Schnizer
(74) *Attorney, Agent, or Firm*—Peter F. Corless; Christine C. O'Day; Edwards & Angell, LLP

(57) ABSTRACT

The present invention provides a human c-Ha-ras proto-oncogene transgenic rat and the methods of the screening of many carcinogens and the screenings of promoters of carcinogenesis and preventive and inhibitory agents of tumors, and additionally enables the analysis of the carcinogenesis mechanism of a number of tumors.

4 Claims, 7 Drawing Sheets

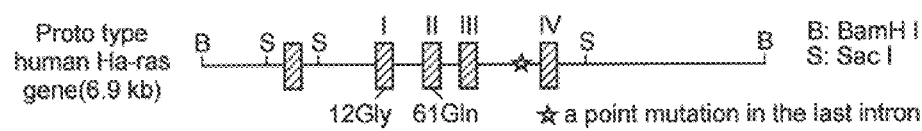
FIG. 1A
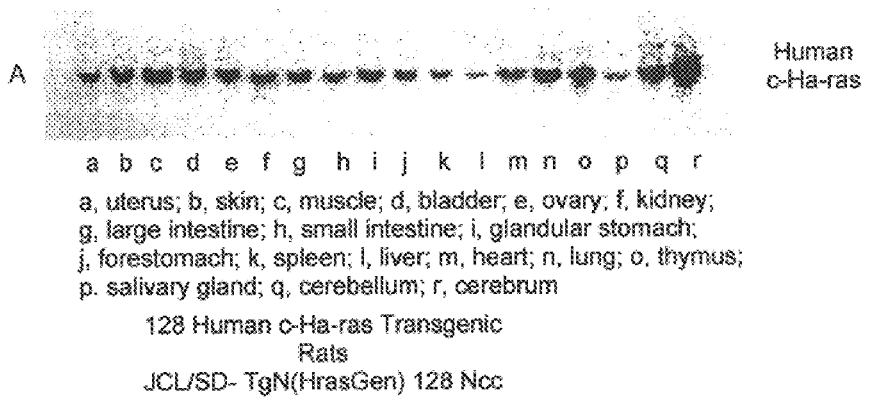
a, uterus; b, skin; c, muscle; d, bladder; e, ovary; f, kidney;
g, large intestine; h, small intestine; i, glandular stomach;
j, forestomach; k, spleen; l, liver; m, heart; n, lung; o, thymus;
p, salivary gland; q, cerebellum; r, cerebrum
128 Human c-Ha-ras Transgenic
Rats
JCL/SD- TgN(HrasGen) 128 Ncc
FIG. 1B

Evaluation of RFLP Sensitivity by DNA Dilution

TRANSGENIC RAT WITH HUMAN NORMAL TYPE C-HA-RAS GENE

The present application claims the benefit of Japanese Patent Application No. JP 10-62130, filed Feb. 25, 1998.

BACKGROUND OF THE INVENTION

1. Field of the Invention

The present invention relates to a human c-Ha-ras proto-oncogenes transgenic rat, and a method for screening carcinogens, promoters of carcinogenesis, and preventing and inhibitory agents of carcinogenesis by using the present gene-engineered rat.

2. Description of the Background Art

The activated type of c-Ha-ras oncogene is detected at a high frequency in various human cancer tissues. A mouse carrying human c-Ha-ras proto-oncogene transgene has already been created and known as rasH2 mouse by Katsuki et. al., who have examined the relation between carcinogenesis and the activation of the transgene as well as the endogenous mouse Ha-ras gene. Their studies of the usefulness of the mouse as an animal for short-term screening of carcinogens are under way. However, organs in which tumor develop are limited to the lung, the skin, the forestomach and tumor induction in many other important organs such as gastrointestinal tracts, urogenital organs and endocrine organs is not satisfactory. Therfore, the transgene rasH2 mouse could not be used as a tool for the analysis of carcinogenesis and detection of carcinogens inducing tumors in such organs. A new animal model to conquer such problem has been desired.

For studies of chemical carcinogenesis, rats rather than mice are more frequently used for various reasons. In the liver carcinogenesis models, a variety of enzyme-altered condition has been studied for their relevance to carcinoma development. For example, an immunohisto-chemically demonstrable enzyme marker, glutathione S-transferase placental form (GST-P) has been utilized for the idetification of liver preneoplastic focal lesions. In contrast, no equivalent markers for preneoplastic foci are available for mice. Furthermore, unlike mice, mammary cancers in rats can be rapidly induced by N-metyhl-N-nitrosourea (MNU) administration without involvement of viral etiology. So far, only limited number of transgenic rats have been reported for studying carcinogenesis. Rats containing an albumin-promoter-fused to the simian virus 40 T antigen gene have been used to investigate GST-P expression in preneoplastic foci in the liver induced by the transgene and another transgenic rat containing the GST-P promoter fused to the chloramphenicol acetyltransferase gene has been analyzed to study regulation of GST-P transcripts in rat liver carcinogenesis.

Analysis of bladder carcinogenesis by use of rat superficial bladder cancer model induced with N butyl-N-(4-hydroxybutyl)nitrosoamine (BBN) can be performed because of its recombinant to humans and therefore, such studies are possible by use of human c-Ha-ras proto-oncogene transgene rat.

As has been described above, the human c-Ha-ras proto-oncogene transgenic rat has many advantages for not only screening of carcinogens and screening of promoters but also preventive and inhibitory agents of carcinogenesis.

We have generated transgenic rats using same gene construct employed for generation of human c-Ha-ras proto-oncogene transgenic mice, which has no mutations in the protein coding regions and no ability to transform NIH3T3 cells. In order to determine their susceptibility to mammary carcinogenesis, human c-Ha-ras proto-oncogene transgenic rats (Hras128 rats) were treated with MNU. Multiple large mammary carcinomas developed all rats 8 weeks after the carcinogen application. Gene mutational analyses indicated that transgene mutation did not play a major role in the enhancement of the carcinogen susceptibility, in contrast to the observation in non-transgenic rats.

SUMMARY OF THE INVENTION

The present invention relates to a human c-Ha-ras proto-oncogene transgenic rat (the term "Hras102" or "Hras128" may be used herein). Additionally, the present invention relates to a method for screening a carcinogen, a promoter as well as preventive and inhibitory agents of carcinogenesis,

BRIEF DESCRIPTION OF THE DRAWINGS

FIG. 1A, the upper column shows the structure of the human c-Ha-ras proto-oncogene; and FIG. 1B, the lower columns two show the mRNA expression of the transgene in individual organs the transgenic rat, wherein "a" represents uterus; "b" represents skin; "c" represents muscle; "d" represents bladder; "e" represents ovary; "f" represents kidney; "g" represents large intestine; "h" represents small intestine; "i" represents glandular stomach; "j" represents forestomach: "k" represents spleen;

"l" represents liver; "m" represents heart; "n" represents lung; "o" represents thymus; "p" represents salivary gland; "q" represents cerebellum; and "r" represents cerebrum.

Figure 2:
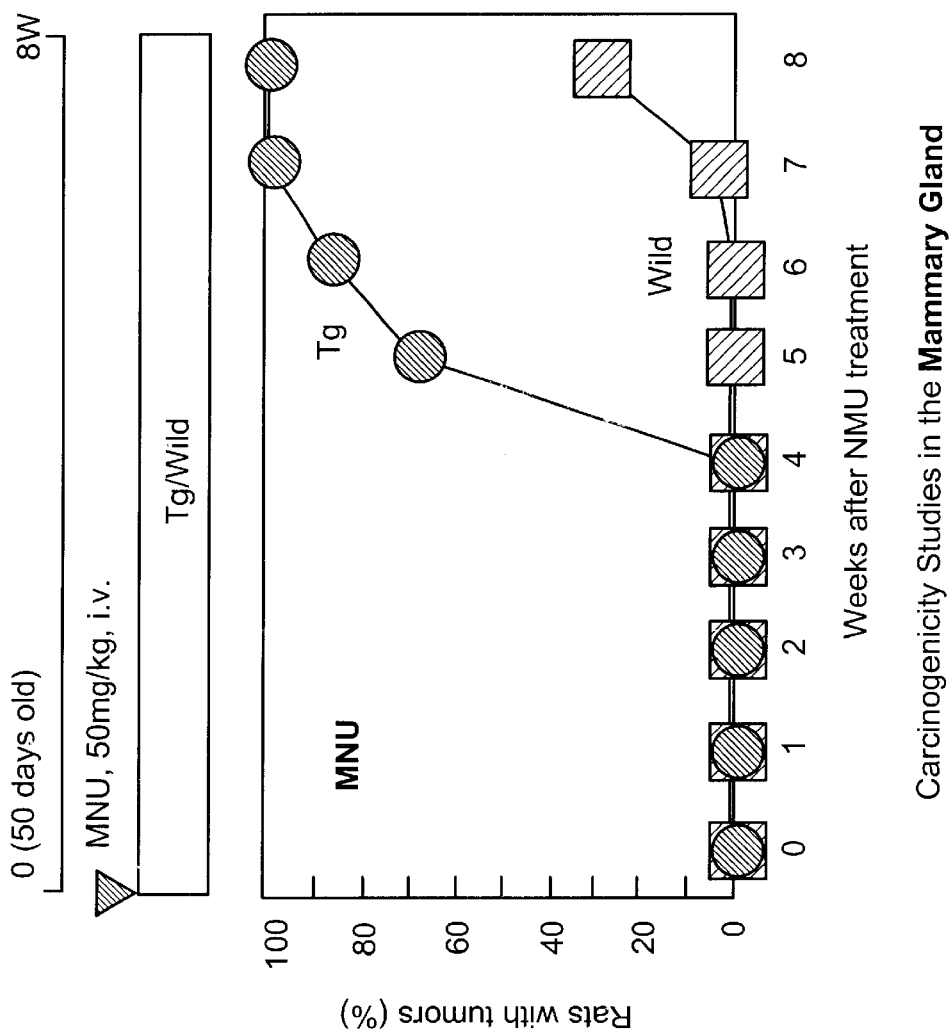

FIG. 2 shows the high susceptibility to MNU administration in mammary gland carcinogenesis of the Hras128 rat.

Figure 3:
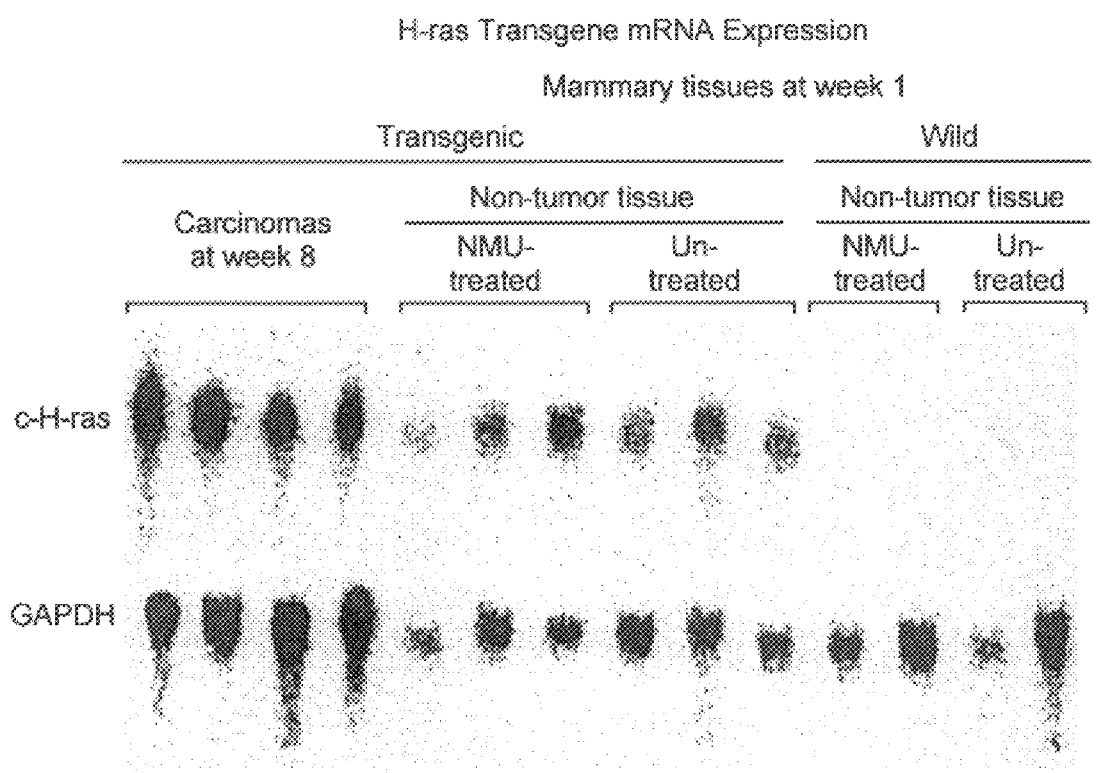

FIG. 3 shows the expression of the human c-Ha-ras proto-oncogene mRNA at the tumor lesions and normal tissue in the Hras128 rat, demonstrated by northern blotting.

Figure 4:
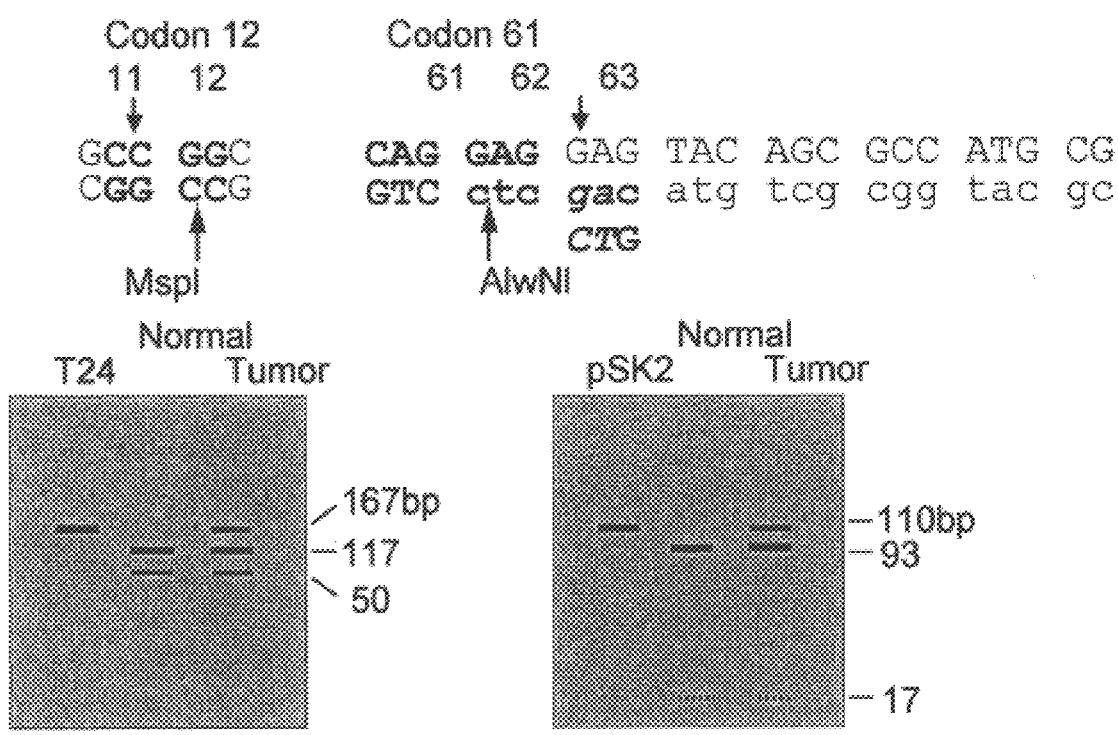

FIG. 4 shows the schematic presentation of RFLP analysis of codon 12 and codon 61 of human c-Ha-ras gene.

Figure 5:
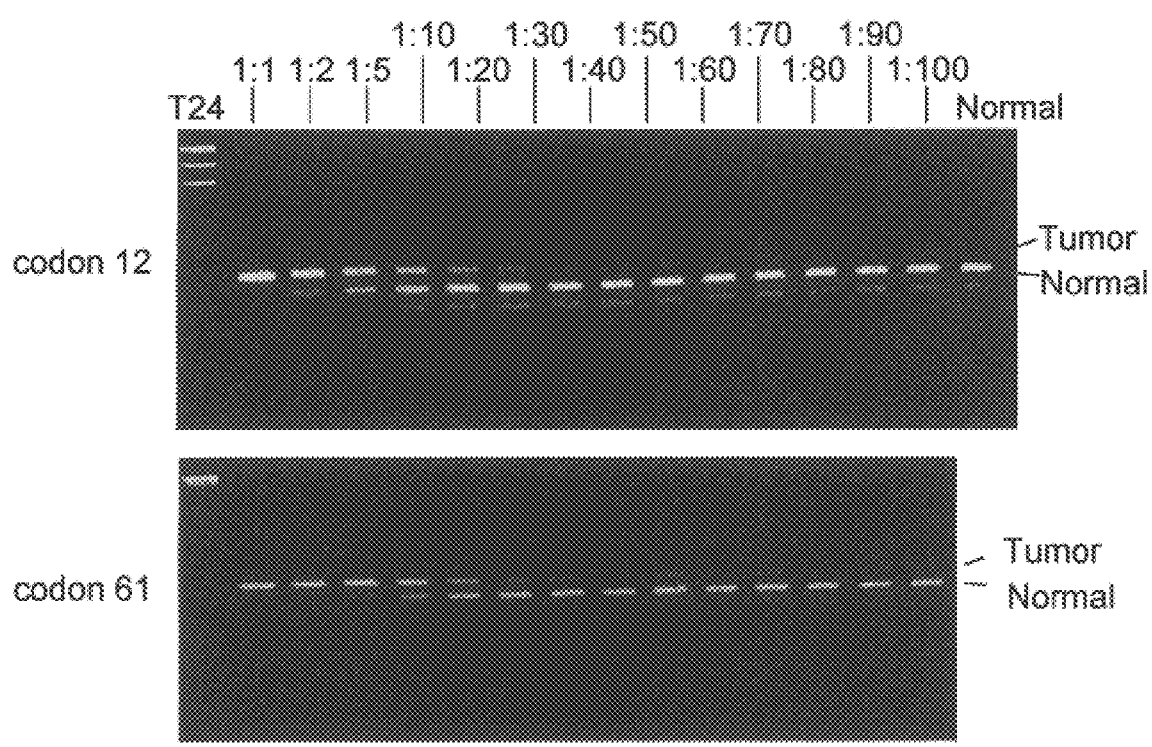

FIG. 5 shows the evaluation of RFLP sensitivity by DNA dilution. The dilution was expressed as "carcinoma cell:normal fibriblart" ratio.

Figure 6:
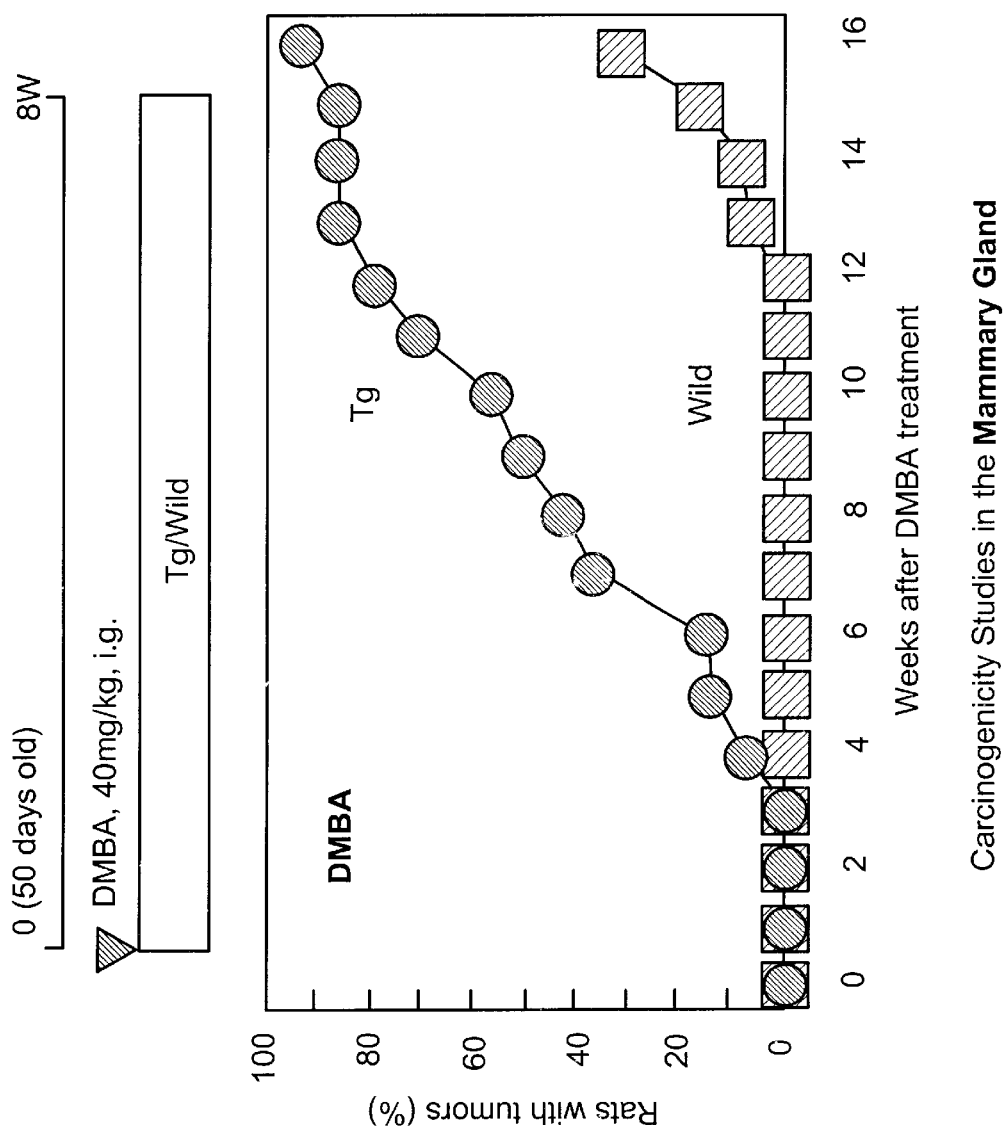

FIG. 6 shows the high susceptibility to DMBA administration in mammary gland carcinogenesis of the Hras 128 rat.

Figure 7:
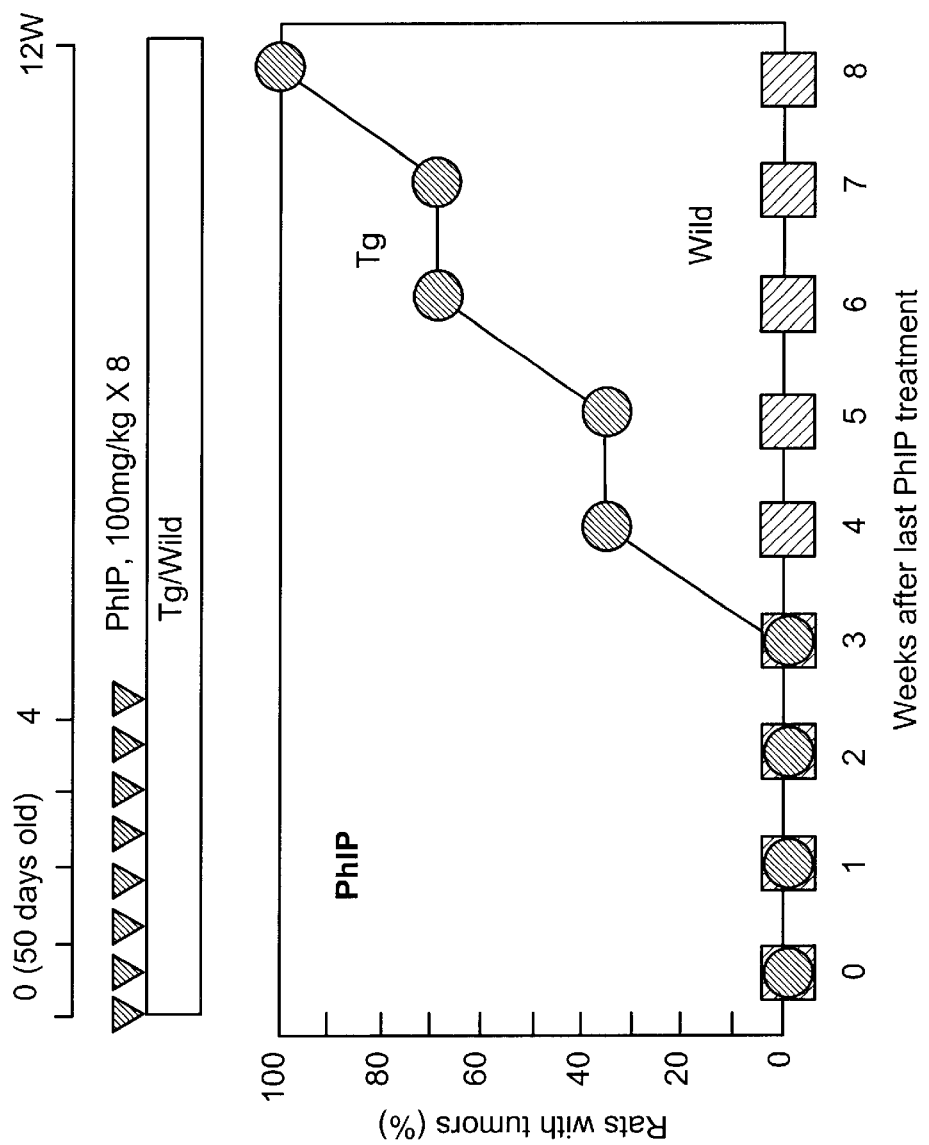

FIG. 7 shows the high susceptibility to PhIP administration in mammary gland carcinogenesis of the Hras 128 rat.

DETAILED DESCRIPTION OF THE INVENTION

The human c-Ha-ras proto-oncogene to be used in accordance with the present invention can be prepared by a known method developed by the present inventors (Sekiya et. al., *Japanese Journal of Cancer Research*. Vol.76, pp.851–855).

FIG. 1, the upper column shows the structure of human prototype c-Ha-ras gene to be transferred. The gene has a 6.9 kb length. "B" and "S" at the right end in this figure shows the sites of restriction enzymes BamHI and SacI, respectively. Additionally, the symbol closed star shows a site of the last intron, where point mutation presents.

For the establishment of transgenic rats, any other strain can be used, however, SD rat may be useful. Also, rats of other strains may be used.

Although as the method for introducing the gene into such rats, known methods such as microinjection method, a method by means of retrovirus, a method by means of embryonic stem cell can be appropriately used. However, microinjection method is the most reliable. Briefly the human c-Ha-ras proto-oncogene was injected into fertilized eggs and then the eggs were transferred into the oviduct of a pseudo-pregnant rat to raise and deliver the fetus.

The human c-Ha-ras proto-oncogene was transmitted into the transgenic rat progeny in such a stable manner that the expression of the gene was observed in all of the organs.

FIG. 1, the lower column A illustrates the expression of mRNA of the transgene in the individual organs by Northern blotting. In the figure, each alphabet represents each individual organ; "a" represents uterus; "b" represents skin; "c" represents muscle, "d" represents bladder; "e" represents ovary; "f" represents kidney; "g" represents large intestine; "h" represents small intestine; "i" represents glandular stomach; "j" represents forestomach; "k" represents spleen; "l" represents liver; "m" represents heart; "n" represents lung; "o" represents thymus; "p" represents salivary gland; "q" represents cerebellum; and "r" represents cerebrum. FIG. 1, the lower column B shows the expression of GAPDH as the controle of expression of mRNA in the transgenic rat.

By use of the Hras128 rat of the present invention, preventive and inhibitory agents of carcinogenesis can be detected by transplacental administration of test compounds.

When a known mammary carcinogen N-methyl-N-nitrosourea (MNU) Is administered to the inventive rat, for example, mammary gland tumor are induced at high frequencies for a short term, as shown in FIG. 2.

It has been reported recently that a cell with the point mutation of Ha-ras codon 12 (GGA to GAA) is present in normal mammary gland, and attention is accordingly focused on the relation between the MNU treatment and the Ha-ras point mutation in the carcinogenesis in rat mammary gland, but the real mechanism has not yet been elucidated. Therefore, the inventive rat may also be exceedingly useful for the elucidation of the carcinogenesis mechanism of such respect.

The results of the analysis of the mechanism of MNU induced carcinogenesis by using the rat of the present invention are now summarized as follows.

1. Generation of Human c-Ha-ras Pronto-Oncogene Transgenic Rats

Injection of the human c-Ha-ras proto-oncogene DNA construct into protonuclei of a total of 1145 rat sertilized eggs, gave rise to 211 potential transgenic embryos, and two founder rats were obtained. Southern blotting analysis revealed that one line had three copies (Hras 128 rat) carrying and the other line had one copy (Hras 102 rat). The transgenes of the rat having three copies were transmitted to the next generations stably and expression of the gene was detected in all organs examined, including the mammary glands, by Northern blotting (FIG. 1). The rat strain was named officially as JCL/SD-TgN (H-rasGEN) 128Ncc (Hras128). However, expression of the transgene in the line of rats with one copy (Hras102) was no longer detectable after two generations. Therefore, only the Hras128 rats were used for the following experiments.

2. Susceptibility Study for MNU Induction of Mammary Carcinogenesis

Hras128 transgenic rats proved highly susceptible to MNU induction of mammary carcinogenesis. Five weeks after a single injection of MNU, multiple mammary tumors were detected by palpation in Hras128 transgenic rats whereas none were present in non-transgenic littermates of the same age (FIG. 2.

By the end of week 8, all Hras128 transgenic rats had developed large multiple tumors with a tendency for decreased body weights and a moribund condition. Therefore all the rats were killed at this time point. The histological appearance of the tumors was of solid tubular adenocarcinomas and did not differ from typical mammary tumors induced in non-transgenic rats. No other macroscopic or microscopic lesions were observed either transgenic or non-transgenic rats at 8 weeks after MNU treatment. Without exposure to the carcinogen, no tumors or abnormalities in the transgenic rats were noted within the experimental period. However, a long-term study for the analysis of spontaneous tumor incidence in the transgenic rats is underway, and it was found that mammary carcinomas and skin papillomas were relatively frequent after 1 year.

3. Mutation Analysis of the Ha-ras Genes in Mammary Tumors by PCR-SSCP

Single-stranded DNA confirmation polymorphism (SSCP) analysis is able to be performed according to the followings; T. Sekiya. Protein, Nucleic Acid, Enzyme, vol. 41, No. 5, 539, 1996.

Possible mutations in exons 1 to 4 of the human Ha-ras proto-oncogene and exons 1 and 2 of the endogenous gene were examined by PCR-SSCP analysis. Using human or rat specific primers, only two bands appeared on the gals. With common primers (cHras21F and cHras21R) for Ha-ras exon 2 of both man and rats, four bands were detected. Human or rat specific bands were identified by signals from normal DNA of the transgenic and non-transgenic rats. DNA from T24 having a mutation in human Ha-ras of codon 12, GGC to GTC and that from pSK2 having a mutation in the codon 61, CAG to CTG, gave clearly mobility shifted bands in the assays (FIG. 4). However, a GGC to GAC mutation of the transgene enriched by PCR after RFLP analysis as described below, which was frequently observed in tumors induced by MNU in human Ha-ras proto-oncogene transgenic mice, could not be detected by SSCP -PCR analysis. In 44 tumors from Hras128 transgenic rats treated with MNU, mutations were not detected in exons 1 to 4 of the introduced human and endogenous c-Ha-ras genes under any of four SSCP conditions (at 4 or 20° C., with or without 5% glycerol) (Table 1). In contrast, a relatively high frequency (6 of 21 tumors of non-transgenic rats (28.6%) of GGA to GAA mutations in codon 12 of the endogenous Ha-ras gene was detected in mammary carcinomas of non-transgenic using PCR-SSCP analysis followed by direct sequencing (Table 1).

TABLE 1 c-Ha-ras Mutations in MNU-Induced Mammary Tumors

| | No. of Tumors Examined | Transgene (Human) Exons [a] | | | | Endogenous (Rat) Exons [b] | |
|---|---|---|---|---|---|---|---|
| | | 1 (Codon 12) | 2 (Codon 61) | 3 | 4 | 1 | 2 |
| Hras 128 | 44 | 38 [c] (86.4%) | 0 | 0 | 0 | 0 | 0 |
| Wild | 21 | — | — | — | — | 6 [d] (28.6%) | 0 |

[a] From both RFLP and SSCP analyses.
[b] From SSCP analysis.
[c] 34, GGC to GAC; 3, GGC to GTC; 1, GGC to AGC
[d] All were GGA to GAA in codon 12.

4. Mutation Analysis by RFLPs

RFLP analysis is able to perform according to the followings; Nagase, et al., Protein, Nucleic Acid, Enzyme, vol. 41, No. 5, 564, 1996).

Thirty-eight out of 44 tumors gave a Mspl resistant band which indicated that these tumors contained mutations in codon 12 of the transgene. The intensity of the mutant bands varied among the samples, two being strong and thirty-four tumors being moderate or slight. Evaluation of sensitivity of this RFLP analysis, with wild (normal liver) and mutant (T24) DNA fragments mixed in various ratios, confirmed detection of very small proportion of mutation at 1 mutant in 100 wild type sequences. Based on band intensities, it was estimated that the strong bands for 2 tumors may contained around 10% mutant PCR fragments, the moderate bands about 2 to 5% mutants, and a faint band approximately 1 to 2% routants. Direct sequencing of the mutant bands revealed that 34 tumors contained GGC to GAC mutation, 3 GGC to GTC, and 1 a GGC to AGC mutation. With RFLP designed for exon 2, no mutations were detected in any of the 44 tumors (see Table 1).

5. Subcloning and Sequencing Analysis

Amplification of exon 1 from 4 tumors (758M, 761G, 772B, 773H), subcloning to plasmids, sequencing of individual DNAs from around 50 colonies per tumor revealed 6 out of 51 clones for 758M to be mutants and, all GGC to AGC in codon 12. GAC mutants were observed with one out of 47 for 761G and three of 51 for 773H. However, all 47 clones for 772B had a wild-type sequence although RFLP analysis, indicated this tumor to have a GAC mutation in minor populations (Table 2).

TABLE 2

Mutation Analysis of MNU-induced Mammary Tumors in Hras 128 Rats by PCR-Subcloning and Sequencing of Transgene Exon 1

| Tumor name | No. of clones examined | No. of mutant clones | Calculated percentage of tumor cells with mutations [a] Normal cell content | | | Mutant sequence of codon 12 |
|---|---|---|---|---|---|---|
| | | | 0% | 20% | 50% | |
| 758M | 51 | 6 | 35.3%[a] | 44.1% | 70.6% | GGC to AGC |
| 761G | 47 | 1 | 6.4% | 8.0% | 12.8% | GGC to GAC |
| 772B | 47 | 0 | — | — | — | — |
| 773H | 51 | 3 | 17.6% | 22.1% | 35.3% | GGC to GAC |

[a] Percentage of mutated tumor cells (No. of mutant clones / No. of clones examined × 3 copies %)

For example, the mutation GGC to AGC was detected in 6 clones of the screened 51 clones in the tumor cell 758M. On the assumption that the ratio of normal cell contamination to this tumor cells is 0, 20 or 50% (the ratio of normal cell contamination at 50% scarcely occurs in the lacteal tumor at the present experiment, and it is estimated that the ratio will be far lower in reality), the ratio of mutant cell contamination per one tumor cell is 35.3, 44.1 or 70.6% in this order, which is calculated according to a formula; frequency of gene mutation by PCR-subcloning (mutant clones/screened clones)×3 (copy number of transferred human c-Ha-ras proto-oncogene)×ratio of normal cell content.

Even if it is assumed that the normal cell content is 20% which is a considerably larger value, the ratio of the human c-Ha-ras proto-oncogene mutation per one tumor cell is 50% at maximum or smaller. Therefore, it is indicated that the mutation of the ras gene does not play a primary role in the carcinogenesis of the present transgenic rat.

By using the Hras128 rat of the present invention, however, it is possible to study the role of the transgene in carcinogenesis because of higher incidence of spontaneous tumor in various organs, in which over expression of the human c-Ha-ras ptoro-oncogene may be responsible.

Additionally, the frequency of spontaneous tumor was examined in the Hras128 rats. The results are shown in Table 3.

TABLE 3

Spontaneous Macroscopic Tumors in c-Ha-ras Transgenic Rats[a] after 78 weeks

| Strain | total No. of rat | No. of rats with tumors (%) | | |
|---|---|---|---|---|
| | | Mammary gland | Skin papilloma | Spleen (sarcoma) |
| Tg 128 female | 29 | 16 (55.2)[b] | 1 (3.4) | 3 (10.3) |
| Wild 128 female | 38 | 6 (15.8) | 0 | 1 (2.6) |
| Tg 128 male | 37 | 10 (27) | 15 (40.5)[c] | 1 (2.7) |
| Wild 128 male | 41 | 5 (12.2) | 2 (4.9) | 0 |

[a] JCL/SD-TgN(HrasGen)128Ncc.
[b] $P < 0.0017$.
[c] $P < 0.0001$.

With regard to yield of supontaneous tumors, at age 78 weeks after birth, incidence of mammary tumor in females and skin tumor in males, the latter rarely occurs in rats, were significantly increased in the Hras128 rats than in the wild type rats. Skin carcinogenesis model has been conventionally established only in mouse, therefore the Hras128 model can also be utilized for the analysis of skin tumor development in the rat.

It is thus indicated that the human c-Ha-ras proto-oncogene rat of the present invention has the following characteristic properties.

(1) Characteristic Properties of Spontaneous Tumor

A. The occurrence of mammary tumor in the female transgenic rats significantly increases, as compared to the wild type.

B. Skin papilloma which very rarely occurs in normal rats occurs at a high frequency in the male transgenic rats. The rats can be used as rat skin carcinogenesis models.

(2) Application for the Screening of Preventive Agents of Carcinogenesis

A. The transgenic rat is effective for the screening of a substance preventing or inhibiting the farnesylation of the protein generated by the ras gene.

Additionally, the effect of inhibitory agents of carcinogenesis can be determined at early stage.

(3) Application to Carcinogenicity Testing of Environmental Compounds

A. Through trans-placental administration of ethylnitrosourea into the transgenic rat, the occurrence of tumors in the central nervous system, kidney, skin, etc. significantly increases within a short period.

B. The action of transplacental as well as non-transplacental carcinogens and its modifying agents can be determined within a short period, by using the transgenic rat. In other words, not only research works for elucidating the mechanism of carcinogenesis but also the screening of carcinogens, preventive and inhibitory agents of carcinogenesis can be performed.

DESCRIPTION OF THE PREFERRED EMBODIMENTS

The present invention will now be described in examples, but the present invention does not be limited to these examples.

Example 1

By microinjection, human c-Ha-ras proto-oncogene was transgened, together with its promoter/enhancer regions into a fertilized eggs from SD rats, then transferred into the sallopian tube of a pseudo-pregnant foster mother to raise the fetuses and deliver pups.

Two strains of gene could be transgened, Hras102 and Hras128 rats carrying one copy and three copies respectively. The transgene was transmitted to their progenies in a stable manner. The transgene expression was confirmed in almost all organs, as shown by Nothern blotting in FIG. 1.

Example 2

MNU, at a dose of 50 mg/kg, was intravenously injected into Hras128 and wild type rats, at 50 days old, to perform histopathological examination of the incidence of mammary tumor and to screen the presence or absence of any point mutation of the transgene and endogenous c-Ha-ras gene.

Mammary tumor became palpable in the Hras128 strain rats, 5 weeks after MNU administration, and then multiple adenocarcinoma developed in all (100%) of the mammary glands of all the transgenic rats at week 8, but that in the wild type rats only 29.2% even at week 8 (see Table 1 and FIG. 2). In 102-strain rats, multiple adenocarcinoma was observed 16 weeks after MNU administration.

The results are shown in Table 4 and FIG. 2.

Herein, "Tg" shown as closed circle in FIG. 2 expresses the rats with the human c-Ha-ras proto-oncogene in the present invention; "Wild" shown with closed square expresses wild type rats (non Tg rats).

TABLE 4

Tumor-Inducing by MNU in Tg Rats

| Strain | MNU Treatment | week after MNU injection | No. of rats | No. of tumor-bearing rats (%) | No. of tumor/rat |
|---|---|---|---|---|---|
| 102 | Performed | 18 | 23 | 20 (87.0) | 5.83 ± 5.31 |
| 102 | — | 18 | 13 | 10 (76.9) | 3.00 ± 2.86 |
| 128 | Performed | 8 | 22 | 22 (100) | 14.0 ± 6.42** |
| 128 | — | 8 | 24 | 7 (29.2) | 0.46 ± 0.93 |

**$P < 0.01$ as compared to wild rat

In 44 tumors from Hras128 rate treated with MNU, mutation of the transgene was not detected by PCR-SSCP analysis. However, by PCR-RFLP analysis 38 (86.4%) tumor showed mutations at codon 12 (Table 1).

Point mutation was detected at 26.8% of the endogenous Ha-ras in the mammary tumors induced by MNU-treatment in wild type rats (non Tg rats). A numerical figure attached to an exon represents the sequential order of the axon in the genome, and the numerical value represents the number (in %) of rats with point mutation detected at the site.

By Northern blotting analysis, the expression of c-Ha-ras gene was examined in Hras128 rats and wild type rats. The band in lower column in FIG. 3 illustrates the control by GAPDH showing that levels of mRNA expression of tumor lesions and normal tissue are almost equal indicating that expression levels are same (FIG. 3).

Thus, it is indicated that the Tg rats were very sensitive to the MNU-induced mammary carcinogenesis.

From the mutation analysis, it is considered that some other gene activation mechanism may be involved except the point mutation of the transgene analyzed.

Example 3

Well established mammary carcinogens, such as 7,14-dimethylbenz[a]anthracene (DMBA) and 2-amino-1-methyl-6-phenylimidazo[4,5-]pyridlne (PhIP) were given to the Hras128 rats in the same manner as in previous reports.

The results are shown in FIG. 6 (DMBA) and FIG. 7 (PhIP). The Hras128 rats exerted high sensitivity to the all those carcinogens.

"Tg" shown with closed circle in FIGS. 6 and 7 expresses the Hras128 rats of the present invention; and "Wild" shown with closed square expresses the wild type rats (non Tg rats).

Table 5 shows the incidence and the number and the size of mammary carcinomas induced by DMBA. The number of tumor indicates number of lesions per rat and the sizes of the tumors indicates their diameter (mm). Table 6 shows the frequency of mutations in the codon 12 or 61 by RFLP analysis.

The Hras128 rat was very sensitive to DMBA, and mutation was detected in the codons 12 (6/20) and 61 (7/20) of the transgene by RFLP analysis.

TABLE 5

Incidence and Multiplicity of Carcinomas Induced by DMBA

| | No. of rats | No. of tumor-bearing rats (%) | No. of tumors/rat | Tumor size (mm) |
|---|---|---|---|---|
| Hras128 | 14 | 13 (92.9)[a] | 9.39 ± 9.79[b] | 12.6 ± 9.22 |
| Wild | 12 | 4 (33.3) | 0.83 ± 1.75 | 13.4 ± 8.20 |

[a]$P < 0.01$;
[b]$P < 0.001$ (Mann-Whitney U-test)

TABLE 6

Frequency of Ha-ras Mutations in Mammary Carcinomas induced by DMBA

| | No. of tumors examined | Transgene (Human) | | | Endogenous (Rat) | |
|---|---|---|---|---|---|---|
| | | Codon 12 | Codon 61 | Total | Exon1 | Exon2 |
| Hras128 | 20 | 6(30%)[a] | 7(35%)[b] | 12(60%) | 0 | 0 |
| Wild | 7 | — | — | — | 0 | 0 |

[a]4 GGC to TGC; 1 GCC; 1 AC/GC/G In addition to 1GGT to GTT In codon 13
[b]4 CAG to CTG; 3 CAG to CAT Incidence of mammary carcinomas by PhIP and the results with gene mutation analysis by RFLP are shown in Tables 7 and 8, respectively.

TABLE 7

Incidence and Multiplicity of Carcinomas Induced by PhIP

| | No. of rats | No. of tumor-bearing rats (%) | No. of tumors/rat | Tumor size (mm) |
|---|---|---|---|---|
| Hras128 | 6 | 6(100)[a] | 9.67 ± 4.76[b] | 9.23 ± 6.21 |
| Wild | 4 | 0(0) | 0 | — |

[a]$P < 0.005$;
[b]$P < 0.01$

TABLE 8

Frequency of Ha-ras Mutations in Mammary Carcinomas Induced by PhIP

| | No. of tumors examined | Transgene (Human) | | | Endogenous (Rat) | |
|---|---|---|---|---|---|---|
| | | Codon 12 | Codon 61 | Total | Exon1 | Exon2 |
| Wild | 20 | 6(30%) | [b]3(23.1%) | 8(61.5)[a] | 0 | 0 |

[a]2 GGC to GAC, 2 GGC to GTC 1 GGC to TGC
[b]3(all) CAG to CAT

The Hras128 rat was also highly sensitive to PhIP, and mutation was detected in the codons 12 (6/20) and 61 (3/20) of the transgene by RFLP analysis.

Example 4

In the same manner as in Example 2, N-methyl-N-nitrosomethylbenzylamine (NMBA) was intravenously administered at 0.5 mg/kg, 17 times, over 5 weeks, to induce esophagus cancer in the Hras128 rats and the wild type rats, and then, the incidence and multiplicity of esophagus tumor (papillomas and carcinomas combined) and the results with gene mutation analysis in these rats are shown in Table 9: the results of the mutation of the codons 12 and 61 are shown in Table 10.

TABLE 9

Incidence and Multiplicity of Esophageal Tumors[a] Induced by NMBA

| | No. of rats male | No. of tumor-bearing rats (%) | No./rat | Size (mm) |
|---|---|---|---|---|
| Hras128 | 19 | 19 (100)[b] | 11.05 ± 7.83[c] | 2.40 ± 1.52 |
| Wild | 18 | 11 (58.3) | 1.67 ± 2.06 | 1.79 ± 1.08 |

[a]Papillomas and carcinomas;
[b]P < 0.005:
[c]P <0.0001

TABLE 10

Frequency of Ha-ras Mutations In Esophageal Tumors Induced by NMBA

| | No. of tumors examined | Transgene (Human) | | | Endogenous (Rat) | |
|---|---|---|---|---|---|---|
| | | Codon 12 | Codon 61 | Total | Exon 1 | Exon 2 |
| Hras 128 | 25 | 19(76%)[a] | 0 | 19(76%) | 2(8%)[b] | 0 |
| Wild | 14 | — | — | — | 8(57.1%)[b] | 0 |

[a]17 GGC to GAC, 1 GGC to TGC, 1 codon 14 GTG to GTA along with codon 12 GGC to GAC
[b]GGA to GAA The Hras128 rat was extremely sensitive to NMBA carcinogenesis in the esophagus, and the mutation of the codon 12 in the transgene was observed at a high incidence (19/25, 76%), and low incidence of endogenous gene mutation (2/25, 8%). Wild type rats also had mutation of their endogenous Ha-ras gene (8/14, 57%). It is indicated that the mutation of the ras gene plays a more significant role in the carcinogenesis in esophagus than in mammary gland cases.

Example 5

In the same manner as in Example 2, 0.05% N-butyl-N-(4-hydroxybutyl)nitrosoamine (BBN) was administered mixed with drinking water to Hras128 rats and the wild type rats for 10 weeks, to induce bladder tumors. The incidences of bladder tumors (papillomas and carcinomas combined) are shown in Table 11, the mutation of the human c-Ha-ras proto-oncogene codons 12 and 61 and endogeneous rat H-ras shown in Table 12.

TABLE 11

Incidence and Multiplicity of Urinary Bladder Tumors[a] Induced by BBN

| | No. of rats female | No. of tumor-bearing rats (%) | No. of tumors/rat | Incidence of carcinomas |
|---|---|---|---|---|
| Hras128 | 20 | 19(95) | 13.2 ± 6.8[b] | 11/14(35.3) |
| Wild | 15 | 15(100) | 7.1 ± 5.2 | 4/13(30.8) |

[a]Papillomas and carcinomas combined;
[b]P < 0.0001

TABLE 12

Frequency of Ha-ras mutations in Bladder Tumors Induced by BBN

| | No. of tumors examined | Transgene (Human) | | | Endogenous (Rat) | |
|---|---|---|---|---|---|---|
| | | Codon 12 | Codon 61 | Total | Exon 1 | Exon 2 |
| Hras128 | 27 | 2(7.4%)[a] | 0 | 2(7.4%) | 0 | 0 |
| Wild | 17 | — | — | — | 1(5.9%)[b] | 0 |

[a]GGC to GAC;
[b]GGA to GAA

The Hras128 rat has a slightly elevated sensitivity to BBN carcinogenesis in the bladder, and by PCR-SSCP analysis, the mutation of the transgene was at Codon 12 observed although at a low frequency (2/27, 7.4%). One wild type rat had mutation of the endogenes Ha-ras gene (1/17. 5.9%).

Example 6

It is known that farnesyl protein transferase inhibitor has antitumor effect (R. Mangues, et al., Cancer Research, 58, 1253–1259, 1998), and similar inhibitory effects of d-limonene on esophageal carcinogenesis was examined in Hras128 rat. The results are shown in Table 13.

TABLE 13

Effects of d-Limonene on MNU-induced Mammary Carcinogenesis in Hras128 Transgenic Rats

| Treatment | No. of rats | No. of tumors/rat | Average size of tumors | |
|---|---|---|---|---|
| | | | mm | mm³ |
| 5% d-Limonene | 9 | 19.4 ± 6.71 | 8.23 ± 4.88 [a] | 269.5 ± 735.5 [a] |
| Basal diet | 8 | 26.4 ± 8.52 | 10.7 ± 7.34 | 637.7 ± 1669 |

[a]P < 0.01

From the results, it is shown that d-limonene has preventive effects of esophageal carcinogenesis.

Thus the Hras128 rats could be utilized for the screening of preventive agents of carcinogenesis in which farnesyl transferase activity is involved.

Example 7

The effects of transplacental administration of carcinogenic substances were examined in offsprings of females and males of Hras128 rats and wild rats.

Transplacental administration of ethylnitrosourea (ENU) was performed and incidence of tumors in many organs of the bearing rats are shown in Table 14.

TABLE 14

ENU-Induced Transplacental Carcinogenesis
In c-Ha-ras Transgenic Rat

| Strain | No. of tumor bearing rat/ total No. of rat | Tumor Incidence | | | | |
| --- | --- | --- | --- | --- | --- | --- |
| | | Mammary gland | Papilloma | Kidney | Spleen | CNS |
| Tg 128 Female | 6/9 | 5/9 | 0 | 2/9 | 2/9 | 3/9 |
| Wild 128 Female | 0/7 | 0 | 0 | 0 | 0 | 0 |
| Tg 128 Male | 8/15 | 4/15 | 3/15 | 6/15 | 0/15 | 6/15 |
| Wild 128 Male | 2/6 | 0 | 0 | 0 | 0 | 2/6 |

In the Hras128 rats, both in females and males, in the present invention, tumor induction in each organ increased by transplacental application of MNU within shorter period than conventional non-transplacental routs of administration.

The rat with the human c-Ha-ras proto-oncogene in the present invention has such advantages that the screening of many environmental carcinogens, tumor promoters of carcinogenesis and preventive agents of mammary, esophageal and urinary bladder and kidney carcinogenesis can thereby be carried out. Such screening has never been performed by use of c-Ha-ras transgenic mice (rasH2 mice) and additionally that the analysis of the carcinogenesis mechanism of a number of tumors type including skin can thereby be performed, and hence, the present invention can provide an industrially useful rat carsinogenesis model.

Embryos of the transgenic rat having the human c-Ha-ras proto-oncogene incorporated into its genome have been deposited in accordance with the Budapest Treaty with the American Type Culture Collection (ATCC) in Manassas, Va. The noted deposit was granted patent deposit number PTA-3482 and a deposit date of Jun. 28, 2001.

Samples of the deposited Hras128 rat will become available to the public and the restrictions imposed on access to the deposits will be removed upon grant of a patent based upon this United States patent application. In addition, the deposit will be replaced if viable samples cannot be dispensed by the Depository.

What is claimed is:

1. A transgenic rat having a human c-Ha-ras proto-oncogene incorporated into its genome wherein said transgenic rat is identical to the rat deposited with the American Type Culture Collection (ATCC) under Deposit No. PTA-3482, wherein the rat is more susceptible to tumor development in organs selected from mammary glands, urogenital tracts, skin, spleen, esophagus, kidney and central nervous system, as compared to a rat not having the human c-Ha-ras proto-oncogene incorporated into its genome.

2. A method for screening a carcinogen or a promoter of carcinogenesis comprising:

administering to the transgenic rat of claim 1 and to a rat not having the human c-Ha-ras proto-oncogene incorporated into its genome the carcinogen or the promoter of carcinogenesis; and comparing the incidence of tumor development between the transgenic rat and the rat not having the human c-Ha-ras proto-oncogene incorporated into its genome.

3. A method for screening preventive and inhibitory agents of carcinogenesis comprising:

administering to the transgenic rat of claim 1 a carcinogen or a promoter of carcinogenesis;

administering to the transgenic rat the preventive and inhibitory agent of carcinogenesis after tumor development; and comparing the incidence of tumors between the transgenic rat administered with the preventive and inhibitory agent of carcinogenesis and a transgenic rat having a tumor but not administered with the preventive and inhibitory agent of carcinogenesis.

4. The offspring or progeny of the transgenic rat of claim 1, wherein the offspring or progeny has inherited the entire genetic complement of c-Ha-ras proto-oncogenes found in the rat of ATCC Deposit No. PTA 3482.

* * * * *